(12) United States Patent
Molz, IV

(10) Patent No.: US 7,621,938 B2
(45) Date of Patent: Nov. 24, 2009

(54) SPINAL IMPLANT CONSTRUCT AND METHOD FOR IMPLANTATION

(75) Inventor: Fred J. Molz, IV, Collierville, TN (US)

(73) Assignee: Warsaw Orthopedic, Inc.

( * ) Notice: Subject to any disclaimer, the term of this patent is extended or adjusted under 35 U.S.C. 154(b) by 449 days.

(21) Appl. No.: 10/757,819

(22) Filed: Jan. 15, 2004

(65) Prior Publication Data

US 2005/0159813 A1    Jul. 21, 2005

(51) Int. Cl.
*A61B 17/70* (2006.01)
*A61F 2/44* (2006.01)

(52) U.S. Cl. .................................. 606/246; 623/17.11
(58) Field of Classification Search .............. 623/17.11; 606/246

See application file for complete search history.

(56) References Cited

U.S. PATENT DOCUMENTS

| | | | |
|---|---|---|---|
| 4,401,112 A | 8/1983 | Rezainan | |
| 4,611,581 A * | 9/1986 | Steffee | 606/61 |
| 4,892,545 A * | 1/1990 | Day et al. | 623/17.11 |
| 5,015,247 A | 5/1991 | Michelson | |
| 5,443,514 A | 8/1995 | Steffee | |
| 5,522,899 A | 6/1996 | Michelson | |
| 5,534,031 A | 7/1996 | Matsuzaki et al. | |
| 5,683,394 A * | 11/1997 | Rinner | 606/86 |
| 5,716,415 A | 2/1998 | Steffee | |
| 5,776,197 A | 7/1998 | Rabbe et al. | |
| 5,888,224 A * | 3/1999 | Beckers et al. | 623/17.16 |
| 6,080,158 A | 6/2000 | Lin | |
| 6,080,193 A | 6/2000 | Hochshuler et al. | |
| 6,099,531 A * | 8/2000 | Bonutti | 606/87 |
| 6,102,950 A | 8/2000 | Vaccaro | |
| 6,106,557 A | 8/2000 | Robioneck et al. | |
| 6,120,503 A * | 9/2000 | Michelson | 606/86 A |
| 6,156,037 A | 12/2000 | LeHuec et al. | |
| 6,190,413 B1 | 2/2001 | Sutcliffe | |
| 6,190,414 B1 | 2/2001 | Young et al. | |
| 6,224,631 B1 * | 5/2001 | Kohrs | 623/17.11 |
| 6,235,059 B1 * | 5/2001 | Benezech et al. | 623/17.16 |

(Continued)

FOREIGN PATENT DOCUMENTS

DE    200 12 236    10/2000

(Continued)

*Primary Examiner*—David H Willse
*Assistant Examiner*—Javier G Blanco

(57) ABSTRACT

A spinal construct and method for implantation is provided which utilizes a spinal implant adapted for insertion within an intervertebral space between an adjacent pair of vertebral bodies, and an elongate member adapted for anchoring to the adjacent vertebral bodies. The spinal implant defines a first transverse dimension and a different second transverse dimension, and is initially inserted into the intervertebral space while in a first operational configuration wherein the first transverse dimension extends along the height of the intervertebral space. The elongate member is anchored to the vertebral bodies to establish and maintain a select height of the intervertebral space. The spinal implant is then rotated to a second operational configuration wherein the second transverse dimension extends along the height of the intervertebral space. The elongate member serves to maintain the select height of the intervertebral space to provide a controlled amount of compression onto the spinal implant and/or a bone growth promoting material contained therein. The elongate member also serves to resist tensile loads during extensional movement of the vertebral bodies to maintain the vertebral endplates in intimate contact with the spinal implant.

24 Claims, 2 Drawing Sheets

U.S. PATENT DOCUMENTS

| | | |
|---|---|---|
| 6,306,170 B2 | 10/2001 | Ray |
| 6,342,074 B1 | 1/2002 | Simpson |
| 6,375,683 B1 * | 4/2002 | Crozet et al. ............. 623/17.15 |
| 6,508,818 B2 | 1/2003 | Steiner et al. |
| 6,533,786 B1 | 3/2003 | Needham et al. |
| 6,616,666 B1 | 9/2003 | Michelson |
| 6,730,125 B1 * | 5/2004 | Lin ......................... 623/17.11 |
| 7,195,643 B2 * | 3/2007 | Jackson .................. 623/17.11 |
| 2001/0020185 A1 | 9/2001 | Ray |
| 2002/0082597 A1 | 6/2002 | Fraser |
| 2002/0107519 A1 * | 8/2002 | Dixon et al. .................. 606/61 |
| 2002/0151893 A1 | 10/2002 | Santilli |
| 2002/0169508 A1 | 11/2002 | Songer et al. |
| 2002/0193880 A1 | 12/2002 | Fraser |

FOREIGN PATENT DOCUMENTS

| | | |
|---|---|---|
| FR | 2 727 005 | 5/1996 |
| FR | 2 764 795 | 12/1998 |

* cited by examiner

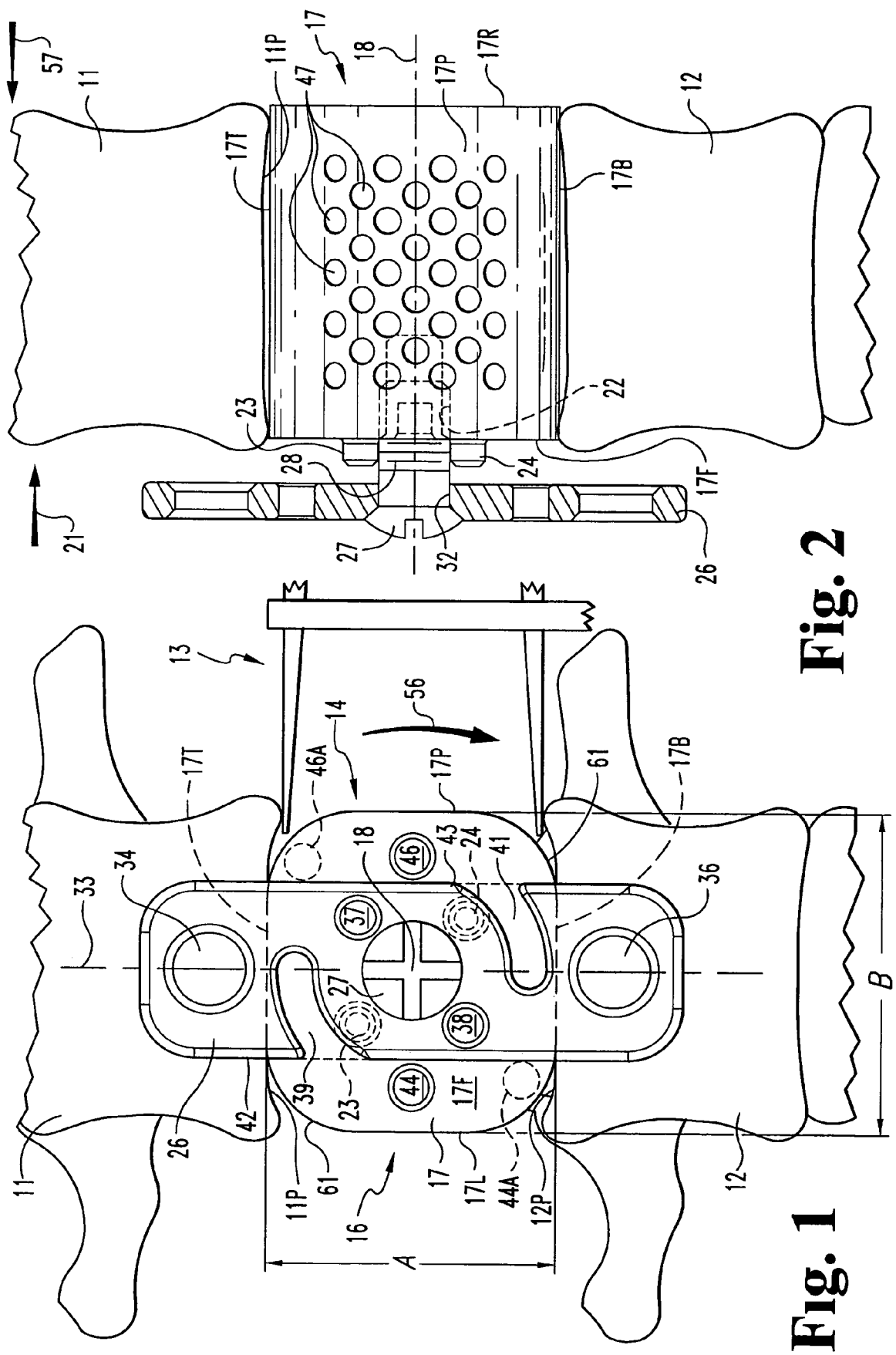

SPINAL IMPLANT CONSTRUCT AND METHOD FOR IMPLANTATION

The present invention relates generally to a spinal interbody implant construct and method for implantation. While the actual nature of the invention covered herein can only be determined with reference to the claims appended hereto, one aspect of the present invention involves insertion of a fusion device into a space between adjacent vertebral bodies from which at least a portion of an intervertebral disc has been removed via a discectomy procedure. Another aspect of the present invention involves rotation of the fusion device within the intervertebral space to establish and maintain controlled compression between the opposing endplates of the adjacent vertebral bodies and the device and/or bone growth promoting material contained within the device. A further aspect of the present invention involves the prevention of an unintentional change of position or orientation of the fusion device subsequent to implantation. There is a general need in the industry to provide an improved spinal implant construct and method of implantation. The present invention meets this need and provides other benefits and advantages in a novel and unobvious manner.

BRIEF DESCRIPTION OF THE DRAWINGS

FIG. 1 is a front elevational view of a device according to one form of the present invention, as inserted within a disc space between adjacent vertebral bodies in a first operational configuration.

FIG. 2 is a side view of the device illustrated in FIG. 1 in the first operational configuration.

DESCRIPTION OF THE ILLUSTRATED EMBODIMENT

Figures 3, 4:
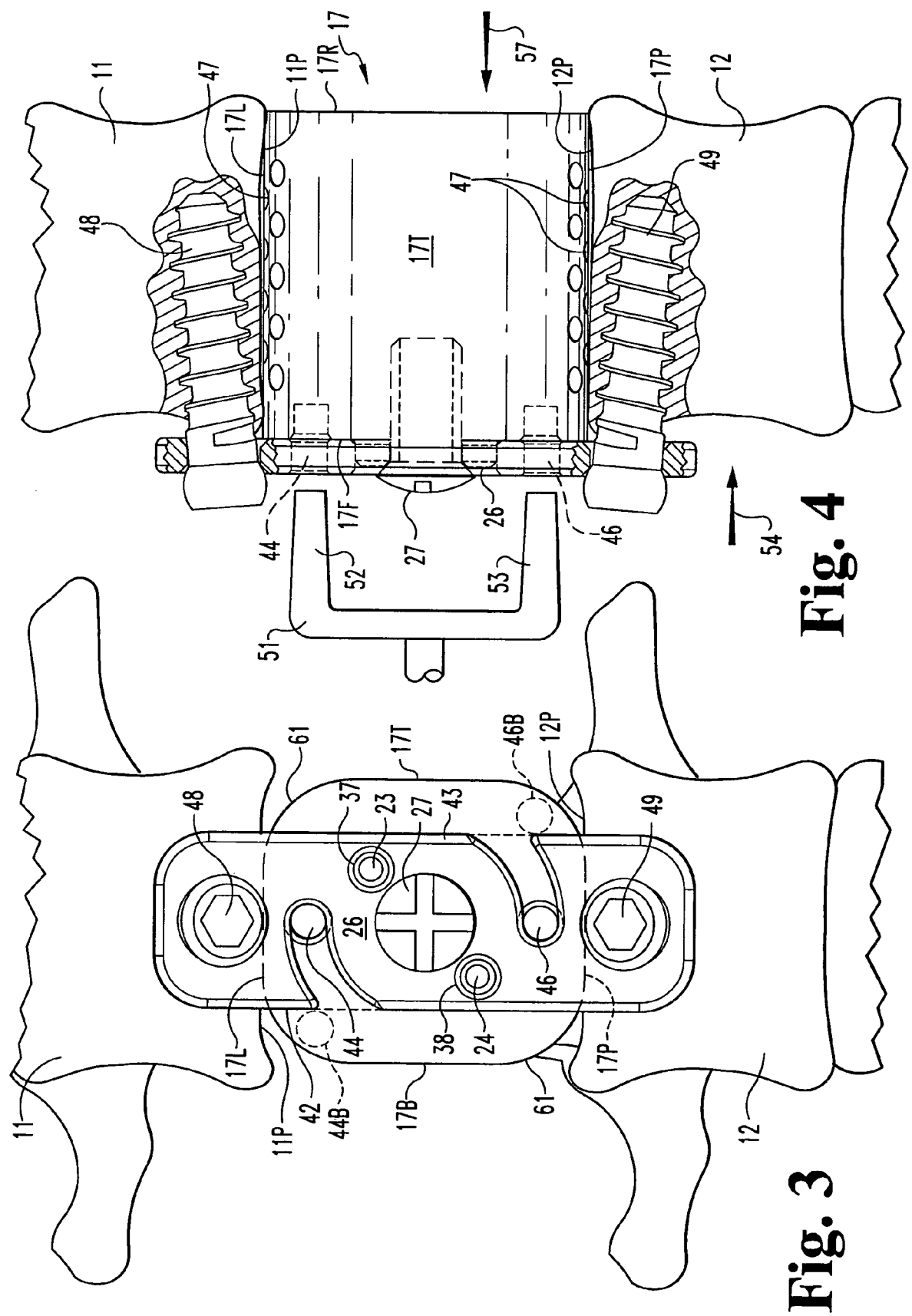
FIG. 3 is a front elevational view of the device illustrated in FIG. 1, as transitioned to a second operational configuration.
FIG. 4 is a side view of the device illustrated in FIG. 3 in the second operational configuration.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Referring to FIGS. 1-4, shown therein is a schematic representation of a portion of the spinal column in which two adjacent vertebral bodies 11 and 12 are held in distraction via a distraction tool 13 to provide an intervertebral space 14 between the vertebral bodies following the removal of at least a portion of a natural intervertebral disc (not shown). However, it should be understood that such distraction of the vertebral bodies via the distraction tool 13 is not essential to practicing the present invention, and in some instances can be avoided.

In a preferred embodiment of the invention, it is desirable to establish fusion between the vertebral bodies 11 and 12. For that purpose, a fusion construct or assembly 16 is provided according to one form of the present invention. In the illustrated embodiment, the fusion construct 16 is generally comprised of a cage portion 17 and an elongate plate portion 26. However, it should be understood that other configurations of the fusion construct 16 are also contemplated as falling within the scope of the present invention. For example, in other embodiments of the invention, the cage portion 17 can be configured as a spacer-type device or any other type of intervertebral implant. Additionally, in other embodiments of the invention, the elongate plate portion 26 can be configured as a rod, a staple, a cable, a tether, or any other type of elongate member. The components of the fusion construct 16 may be formed from any bio-compatible material such as, for example, titanium, stainless steel or any other suitable material.

In one embodiment of the present invention, the cage portion 17 of the fusion construct 16 extends along a longitudinal axis 18 and has a generally rectangular, parallelepiped configuration including front and rear portions 17F, 17R, left and right side portions 17L, 17P (also referred to as primary portions), and top and bottom portions 17T, 17B (also referred to as secondary portions). However, it should be understood that other shapes and configurations of the fusion cage 17 are also contemplated as falling within the scope of the present invention. For example, the fusion cage 17 can take on an elliptical or semi-elliptical configuration, a cam-like configuration, a polygonal configuration, or any other suitable configuration. The overall height of the cage 17 between the top and bottom portions 17T, 17B (transverse dimension A illustrated FIG. 1) is less than the overall width of the cage 17 between the left and right side portions 17L, 17P (transverse dimension B illustrated in FIG. 1). This dimensional configuration facilitates insertion of the cage 17 into the intervertebral space 14 between the lower endplate 11P of upper vertebral body 11 and the upper endplate 12P of lower vertebral body 12 by simply pushing the cage 17 in the direction of arrow 21 (FIG. 2).

In the illustrated embodiment of the cage 17, the primary side portions 17L, 17P are arranged substantially parallel to one another. However, in an alternative embodiment, the primary side portions 17L, 17P may be angularly offset relative to one another so as to define a taper to accommodate for an offset angle between the upper and lower vertebral endplates 11P, 12P (e.g., to accommodate for a particular lordotic angle associated with portion of the spinal column being treated). Additionally, in the illustrated embodiment of the cage 17, the secondary side portions 17T, 17B are arranged substantially parallel to one another. However, in an alternative embodiment, the secondary side portions 17T, 17B may be angularly offset relative to one another so as to define a taper to facilitate axial insertion of the cage 17 into the intervertebral space 14.

In the illustrated embodiment of the invention, the cage 17 includes features for engaging the plate 26. For example, the cage 17 defines a threaded opening 22 positioned generally along the longitudinal axis 18 which opens onto a front surface of the front end portion 17F. Additionally, the cage 17 includes a first pair of posts 23, 24 projecting axially from the front end portion 17F and radially offset from and located on diametrically opposite sides of the longitudinal axis 18. However, it should be understood that other positions and arrangements of the posts 23, 24 are also contemplated as falling within the scope of the present invention. In one embodiment of the invention, the elorigate plate 26 is selectively engaged with the cage 17 via a fastener 27. However, it should be understood that in other embodiments of the invention, the plate 26 need not necessarily be engaged with the cage 17. In a specific embodiment, the elongate plate 26 is provided with a central passage 32 through which extends a threaded shank 28 of the fastener 27. The threaded shank 28 is in turn threadedly engaged within the opening 22 in the cage 17, as shown in FIG. 2, to securely engage the plate 26 with the cage 17. In a further embodiment of the invention, the plate 26 extends along a longitudinal axis 33 and defines a pair of openings 34, 36 disposed adjacent opposite ends thereof which are configured to receive a respective fastener therethrough, the details of which will be discussed below.

The elongate plate 26 also defines a pair of passages 37, 38 that are radially offset from and located on diametrically opposite sides of the longitudinal axis 18. The passages 37, 38 are sized and positioned so as to receive the respective posts 23, 24 extending from the cage 17 therein. As should be appreciated, the angular orientation of the posts 23, 24 extending from the cage 17 is initially offset 90° from the angular orientation of the passages 37, 38 in the plate 26 when the cage 17 is positioned in the first operational configuration illustrated in FIGS. 1 and 2. However, when the cage 17 is rotated to the second operational configuration illustrated in FIGS. 3 and 4, the posts 23, 24 are aligned with the passages 37, 38. Once rotated to the second operational configuration, tightening of the fastener 27 into the threaded opening 22 in the cage 17 results in displacement of the cage 17 toward the plate 26 and positioning of the posts 23, 24 within the passages 37, 38. However, it should be understood that in another embodiment, tightening of the fastener 27 into the threaded opening 22 in the cage 17 may result in displacement of the plate 26 toward the cage 17 to position the posts 23, 24 within the passages 37, 38.

Positioning of the posts 23, 24 within the passages 37, 38 in turn prevents further rotation and/or lateral displacement of the cage 17 relative to the plate 26. However, it should be understood that the cage 17 and the plate 26 may define other elements or features that interlock with one another to selectively prevent rotational and/or lateral displacement therebetween. For example, in another embodiment of the invention, the cage 17 and the plate 26 may have a splined configuration wherein the cage 17 and the plate 26 define a number of splines that are positionable within a corresponding number of grooves to selectively prevent rotational and/or lateral displacement therebetween. Other interlocking elements or features are also contemplated including, for example, a tongue and groove configuration, or any other interlocking configuration suitable for selectively preventing rotational and/or lateral displacement between the cage 17 and the plate 26.

The elongate plate 26 further defines a pair of curved or arcuate slots 39, 41 extending from opposite edges 42, 43 of the plate 26 and progressing inwardly toward the center of the plate 26 adjacent the longitudinal axis 33. In the illustrated embodiment, the arcuate slots 39, 41 extend along a common radius; however, other slot configurations and arrangements are also contemplated as falling within the scope of the invention. As illustrated in FIG. 1, the front end portion 17F of the cage 17 defines a pair of tool-receiving passages 44, 46. The passages 44, 46 are radially offset from and located on diametrically opposite sides of the longitudinal axis 18 and are positioned generally along the radius of the arcuate slots 39, 41. The tool-receiving passages 44, 46 are sized and positioned so as to receive respective portions 52, 53 of a tool 51 therein (FIG. 4). As should be appreciated, the angular orientation of the tool-receiving passages 44, 46 in the cage 17 is initially offset 90° from the longitudinal axis 33 of the plate 26 when the cage 17 is positioned in the first operational configuration illustrated in FIGS. 1 and 2. However, as the cage 17 is rotated to the second operational configuration illustrated in FIGS. 3 and 4, the tool-receiving passages 44, 46 and the respective portions 52, 53 of the tool 51 received therein are displaced along the arcuate slots 39, 41 in the plate 26 to avoid interference between the tool 51 and the plate 26.

Once rotated to the second operational configuration, the tool 51 may be disengaged from the passages 44, 46 and removed from the surgical site.

In a preferred embodiment of the invention, a bone growth promoting material may be packed within a hollow interior portion of the cage 17 to promote fusion with the adjacent vertebral endplates 11P, 12P. In one embodiment, the primary side portions 17L, 17P of the cage 17 define a number of relatively small diameter fusion openings 47 extending therethrough in communication with the hollow interior of the cage 17. However, it should be understood that various types and sizes of openings may be provided to expose the bone growth promoting material to the vertebral endplates 11P, 12P including, for example, perforations or openings of various sizes and shapes including relatively large slotted openings or windows extending through the primary side portions 17L, 17P of the cage 17. In another embodiment of the invention, at least the primary side portions 17L, 17P of the cage 17 may be formed of a relatively porous material to promote bony on-growth. Additionally, although not specifically shown in the illustrated embodiment of the invention, the secondary side portions 17T, 17B of the cage 17 may be provided with a number of fusion openings and/or may be formed of a porous material to further promote fusion between the adjacent vertebral endplates 11P, 12P and the secondary side portions 17T, 17B of the cage 17.

In one embodiment of the invention, the bone growth promoting material is comprised of a bone graft material, a bone morphogenic protein (BMP), or any other suitable bone growth promoting material or substance including, but not limited to bone chips or bone marrow, a demineralized bone matrix (DBM), mesenchymal stem cells, and/or a LIM mineralization protein (LMP). It should be understood that the bone growth promoting material can be used with or without a suitable carrier. In a further embodiment of the invention, the bone growth promoting material is positioned within the hollow interior of the cage 17 prior to insertion within the space 14 between the adjacent vertebral bodies 11, 12. However, in another embodiment, the bone growth promoting material may be positioned within the hollow interior of the cage 17 subsequent to insertion within the intervertebral space 14.

Having illustrated and described various elements and features associated with the fusion construct 16, reference will now be made to a technique for engaging the fusion construct 16 with the adjacent vertebral bodies 11, 12 according to one embodiment of the invention. However, it should be understood that other techniques and procedures are also contemplated, and that the following technique in no way limits the scope of the present invention.

The vertebral level to be treated is initially identified followed by the removal of at least a portion of the natural intervertebral disc via a total or partial discectomy. The endplates 11P, 12P of the upper and lower vertebral bodies 11, 12 are then prepared using known surgical instruments and techniques (e.g., rotating cutters, curettes, chisels, etc.). In some instances, it may be desirable to remove an amount of cortical bone from the vertebral endplates 11P, 12P to facilitate passage of the leading corners of the cage 17 as the cage is rotated about the longitudinal axis 18. As discussed above, the upper and lower vertebral bodies 11, 12 may be held in a distracted condition via the distraction tool 13 to provide an open space 14 between the vertebral bodies following the discectomy. Depending on the preference of the surgeon, the distraction tool 13 may be removed or left in place throughout the remainder of the surgical procedure.

The cage 17 used for treatment of the spinal column is selected such that the transverse dimension A between the secondary side portions 17T, 17B is sized to allow for insertion of the cage 17 within the intervertebral space 14 between the vertebral endplate 11P, 12P while in the first operational configuration illustrated in FIGS. 1 and 2. Additionally, the transverse dimension B between the primary side portions 17L, 17P is selected to provide a select height of the intervertebral space 14 between the vertebral endplate 11P, 12P and to impart a desired amount of compression onto the cage 17 and/or the bone growth promoting material contained therein following rotation of the cage 17 to the second operational configuration illustrated in FIGS. 3 and 4.

After selection of the appropriately sized cage 17, the cage 17 is inserted into the intervertebral space 14, preferably via an anterior surgical approach, with the secondary side portions 17T, 17B facing and arranged substantially parallel with the vertebral endplates 11P, 12P. However, in other embodiments, the cage 17 may be inserted into the intervertebral space 14 via other surgical approaches, such as, for example, via a posterior surgical approach. Following insertion of the cage 17 within the intervertebral space 14, the elongate plate 26 is attached to the upper and lower vertebral bodies 11, 12 via a pair of fasteners or bone screws 48, 49 (FIGS. 3 and 4) that are received through the openings 34, 36 extending through the end portions of the plate 26. Attachment of the plate 26 to the vertebral bodies 11, 12 preferably occurs subsequent to engagement of the plate 26 with the cage 17 via the threaded fastener 27 (FIG. 2). However, it should be understood that in other embodiments, the elongate plate 26 may be attached to the vertebral bodies 11, 12 prior to engagement with the cage 17. As shown in FIGS. 3 and 4, the elongate plate 26 extends between the vertebral bodies 11, 12 and bridges the intervertebral space 14.

With the elongate plate 26 secured to the vertebral bodies 11, 12 and with the cage 17 engaged with the plate 26 (but still rotatable relative thereto), a tool 51 including axial prongs 52 and 53 (FIG. 4) is advanced in the direction of arrow 54 until the tool prongs 52, 53 are inserted into the corresponding tool receiving opening 44, 46 in the cage 17. The tool 51 is then rotated in a clockwise direction (in the direction of arrow 56 in FIG. 1) to correspondingly rotate the cage 17 90° from the first operational configuration/orientation illustrated in FIGS. 1 and 2 to the second operational configuration/orientation illustrated in FIGS. 3 and 4. Once rotated to the second operational configuration/orientation, the primary side portions 17L, 17P intimately engage the vertebral endplates 11P and 12P of the upper and lower vertebral bodies 11, 12, with the secondary side portions 17T, 17B arranged perpendicular to the vertebral endplates 11P, 12P.

As discussed above, as the cage 17 is rotated from the first operation configuration to the second operational configuration, the tool prongs 52, 53 are displaced through the arcuate slots 39, 41 in the plate 26 to avoid interference between the tool 51 and the edges 42, 43 of the plate 26. However, in an alternative embodiment of the invention, it is possible to omit the arcuate slots 39, 41 from the plate 26 via relocation of the tool receiving openings 44, 46 to the alternative locations 44A and 46A shown in dashed lines in FIG. 1. As should be appreciated, with the tool receiving openings 44, 46 positioned at locations 44A and 46A, rotation of the cage 17 to the second operational configuration illustrated in FIG. 3 would avoid any interference between the tool prongs 52, 53 and the lateral edges 42, 43 of the plate 26.

As discussed above, the transverse dimension B between the primary side portions 17L, 17P is selected to impart a desired amount of compression onto the cage 17 and/or the bone growth promoting material contained therein following rotation of the cage 17 to the second operational configuration. The plate 26 extending between the vertebral bodies 11, 12 serves to prevent the vertebral bodies 11, 12 from distracting or separating apart during rotation of the cage 17 to the second operational configuration, thereby controlling the amount of compression exerted onto the cage 17 and/or the bone growth promoting material contained therein. As should be appreciated, the distance between the screw-receiving openings 34, 36 in the plate 26 controls the height of the intervertebral space formed between the vertebral endplate 11P, 12P, and also serves to control the amount of compression exerted onto the cage 17 and the bone growth promoting material contained therein by the vertebral endplate 11P, 12P. The plate 26 therefore functions in a strut-like manner to control the amount of compression exerted onto the cage 17 and the bone growth promoting material. Additionally, the plate 26 may also function to resist tensile loads and/or to limit extension or separation of the vertebral bodies 11, 12 at the surgical site during subsequent patient activity (e.g., during extension of the vertebral bodies 11, 12 adjacent the surgical site).

Following rotation of the cage 17 to the second operational configuration illustrated in FIGS. 3 and 4, the tool 57 may be removed from the passages 44, 46 in the cage 17. Additionally, the fastener 27 is further threaded into the passage 22 in the cage 17, thereby resulting in displacement of the cage 17 in the direction of arrow 57 toward the plate 26 (FIGS. 2 and 4). Displacement of the cage 17 in the direction of arrow 57 in turn results in the positioning of the pins 23, 24 extending from the cage 17 within the passages 37, 38 formed in the plate 26. Positioning of the pins 23, 24 within the passages 37, 38 serves to prevent further rotation and/or lateral movement of the cage 17 relative to the plate 26. Additionally, since the plate 26 is securely engaged to the vertebral bodies 11, 12 via the bone screws 48, 49, positioning of the pins 23, 24 within the passages 37, 38 likewise serves to prevent rotation and/or lateral movement of the cage 17 relative to the vertebral bodies 11, 12.

In one embodiment of the invention, the cage 17 is provided with a transition feature between the primary side portions 17L, 17P and the secondary side portions 17T, 17B to aid in the rotation of the cage 17 between the first and second operational configurations. In the illustrated embodiment, the transition feature comprises a rounded corner 61 defining a convex outer surface (FIGS. 1 and 3). In effect, the rounded corners 61 provide a smooth transition between the primary side portions 17L, 17P and the secondary side portions 17T, 17B. The rounded corners 61 thereby serve to eliminate the sharp corners or edges otherwise associated with the rectangular-shaped cage 17, thereby allowing for rotation of the cage 17 between the first and second operational configurations without undue interference by or disturbance of the adjacent vertebral bodies 11, 12. In the illustrated embodiment, the transition surfaces 61 are semi-cylindrical surfaces and extend the entire length of the cage 17 from the front portion 17F to the rear portion 17R. However, other shapes and configurations of the transition surfaces 61 are also contemplated as would occur to one of ordinary skill in the art. Additionally, although the illustrated embodiment of the cage 17 includes a transition surfaces 61 at each of its four corners, it should be understood that in another embodiment, only the opposite corners of the cage 17 that directly contact the vertebral endplates 11P, 12P during rotation of the cage 17 need necessarily be provided with a transition surface 61.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A spinal construct for engagement with adjacent vertebral bodies, comprising:
a spinal implant comprising an intervertebral fusion device including one or more openings configured to promote fusion with the adjacent vertebral bodies, wherein said intervertebral fusion device includes a hollow interior with said openings in communication with said hollow interior, said spinal implant extending along a longitudinal axis and having a first transverse dimension sized for insertion within an intervertebral space between the adjacent vertebral bodies and a second transverse dimension greater than said first transverse dimension and corresponding to a select height of said intervertebral space;
a bone growth promoting material positioned within said hollow interior to facilitate fusion with the adjacent vertebral bodies; and
an elongate member sized to span the intervertebral space and a plurality of bone anchors extending transversely from said elongate member and into engagement with the adjacent vertebral bodies to establish said select height of the intervertebral space and to maintain said select height as said spinal implant is transitioned from said first transverse dimension to said second transverse dimension along said select height to thereby provide controlled compression of said spinal implant, and wherein said spinal implant is rotatably coupled with said elongate member to allow selective rotation of said spinal implant relative to said elongate member about said longitudinal axis to align said second transverse dimension alone said select height; and
wherein an axially facing portion of said spinal implant defines at least two tool engaging elements to facilitate rotation of said spinal implant within said intervertebral space about said longitudinal axis, wherein said tool engaging elements are positioned diametrically opposite one another relative to said longitudinal axis; and
wherein said elongate member defines a pair of arcuate slots positioned diametrically opposite one another relative to said longitudinal axis, said arcuate slots being sized and configured to receive said tool engaging elements during rotation of said spinal implant about said longitudinal axis.

2. A spinal implant assembly, comprising:
a device adapted for insertion into an intervertebral space between an adjacent pair of vertebral bodies, said device extending along a longitudinal axis and including:
a pair of primary side surfaces spaced apart and arranged generally opposite one another to define a primary transverse dimension; and
a pair of secondary side surfaces spaced apart and arranged generally opposite one another to define a secondary transverse dimension sized for insertion into the intervertebral space, said primary transverse dimension sized greater than said secondary transverse dimension and corresponding to a select height of said intervertebral space;
wherein said device has a substantially rectangular transverse cross section and includes a rounded transitional surface at diagonally opposite corner portions of said device extending between said pair of primary side surfaces and said pair of secondary side surfaces to facilitate rotation of said device within the intervertebral space about said longitudinal axis; and
an elongate member sized to span the intervertebral space and a plurality of bone anchors extending transversely from said elongate member and into engagement with the adjacent vertebral bodies to establish said select height of the intervertebral space and to maintain said select height of the intervertebral space, said device being rotatable relative to said elongate member about said longitudinal axis to align said primary transverse dimension along said select height of the intervertebral space to thereby provide controlled compression of said device; and
wherein said device is rotatably coupled with said elongate member by a fastener including a threaded shank extending through a passage in said elongate member, wherein tightening said fastener interlocks said device with said elongate member to selectively prevent rotational movement of said device relative to said elongate member subsequent to alignment of said primary transverse dimension along said select height of the intervertebral space; and
wherein said device comprise an intervertebral fusion device including a hollow interior with openings extending through said second pair of side surfaces and in communication with said hollow interior; and
further comprising a bone growth promoting material positioned within said hollow interior to facilitate fusion with the adjacent vertebral bodies.

3. The spinal implant assembly of claim 2, wherein said primary transverse dimension is oriented substantially perpendicular to said secondary transverse dimension.

4. The spinal implant assembly of claim 2, further comprising an interlock between said device and said elongate member to selectively prevent at least one of rotational and lateral movement of said device relative to said elongate member subsequent to alignment of said primary transverse dimension along said select height of the intervertebral space.

5. The spinal implant assembly of claim 4, wherein said interlock comprises:
at least one projection portion extending from one of said device and said elongate member; and
at least one aperture defined by another of said device and said elongate member; and
wherein insertion of said at least one projection portion into a respective one of said at least one aperture prevents said at least one of rotational and lateral movement of said device relative to said elongate member.

6. The spinal implant assembly of claim 2, wherein said device comprises a fusion cage.

7. The spinal implant assembly of claim 2, wherein said device has a parallelepiped configuration.

8. A spinal construct for engagement with adjacent vertebral bodies, comprising:
a spinal implant extending along a longitudinal axis and including:
a first pair of side surfaces spaced apart and arranged generally opposite one another to define a first transverse dimension sized for insertion within an intervertebral space between the adjacent vertebral bodies; and
a second pair of side surfaces spaced apart and arranged generally opposite one another to define a second transverse dimension greater than said first transverse dimension and corresponding to a select height of said intervertebral space;

wherein said spinal implant has a substantially rectangular transverse cross section and includes a rounded transitional surface at diagonally opposite corner portions of said spinal implant extending between said first pair of side surfaces and said second pair of side surfaces to facilitate rotation of said spinal implant within the intervertebral space about said longitudinal axis; and an elongate member sized to span the intervertebral space and a plurality of bone anchors extending transversely from said elongate member and into engagement with the adjacent vertebral bodies to establish said select height of the intervertebral space and to maintain said select height of the intervertebral space, wherein said spinal implant is rotatably coupled with said elongate member to allow selective rotation of said spinal implant relative to said elongate member about said longitudinal axis to align said second transverse dimension along said select height of the intervertebral space to thereby provide controlled compression of said spinal implant; and wherein said spinal implant is rotatably coupled with said elongate member by a fastener including a threaded shank extending through a passage in said elongate member, wherein tightening said fastener interlocks said spinal implant with said elongate member to selectively prevent rotational movement of said spinal implant relative to said elongate member subsequent to alignment of said primary transverse dimension along said select height of the intervertebral space; and wherein said spinal implant comprises an intervertebral fusion device including a hollow interior with openings extending through said second pair of side surfaces and in communication with said hollow interior; and further comprising a bone growth promoting material positioned within said hollow interior to facilitate fusion with the adjacent vertebral bodies.

9. The spinal construct of claim 8, wherein said second pair of side surfaces are arranged substantially parallel to one another.

10. The spinal construct of claim 8, wherein said second pair of side surfaces are angled relative to one another to define a taper extending along said longitudinal axis corresponding to the natural lordotic angle between the adjacent vertebral bodies.

11. The spinal construct of claim 8, wherein said first pair of side surfaces are angled relative to one another to define a taper extending along said longitudinal axis to facilitate insertion of said spinal implant within the intervertebral space between the adjacent vertebral bodies.

12. The spinal construct of claim 8, further comprising an interlock between said spinal implant and said elongate member to selectively prevent at least one of rotational and lateral movement of said spinal implant relative to said elongate member subsequent to alignment of said second transverse dimension along said select height of the intervertebral space.

13. The spinal construct of claim 12, wherein said interlock prevents both rotational and lateral movement of said spinal implant relative to said elongate member.

14. The spinal construct of claim 12, wherein said interlock comprises:
   at least one projection portion extending from one of said spinal implant and said elongate member; and
   at least one aperture defined by another of said spinal implant and said elongate member; and
   wherein insertion of said at least one projection portion into a respective one of said at least one aperture prevents said at least one of rotational and lateral movement of said spinal implant relative to said elongate member.

15. The spinal construct of claim 14, wherein insertion of said at least one projection portion into said respective one of said at least one aperture is accomplished by tightening of said fastener.

16. The spinal construct of claim 15, wherein said spinal implant includes a threaded opening; and
   wherein said threaded shank of said fastener is inserted through said passage in said elongate member and is threadingly engaged within said threaded opening in said spinal implant.

17. The spinal construct of claim 14, wherein said at least one projection portion and said at least one aperture each being offset from said longitudinal axis.

18. The spinal construct of claim 14, wherein said interlock comprises:
   at least two projection portions extending from said one of said spinal implant and said elongate member; and at least two apertures defined by said another of said spinal implant and said elongate member; and
   wherein insertion of said at least two projection portions into respective ones of said at least two apertures prevents said at least one of rotational and lateral movement of said spinal implant relative to said elongate member.

19. The spinal construct of claim 8, wherein an axially facing portion of said spinal implant defines at least two tool engaging elements to facilitate rotation of said spinal implant within said intervertebral space about said longitudinal axis.

20. The spinal construct of claim 19, wherein said tool engaging elements are apertures.

21. The spinal construct of claim 19, wherein said tool engaging elements are positioned diametrically opposite one another relative to said longitudinal axis.

22. The spinal construct of claim 8, wherein said intervertebral fusion device is formed of a porous material to facilitate fusion with the adjacent vertebral bodies.

23. The spinal construct of claim 8, wherein said first transverse dimension is oriented substantially perpendicular to said second transverse dimension.

24. The spinal construct of claim 8, wherein said elongate member comprises a plate define a first opening overlapping one of the adjacent vertebral bodies and a second opening overlapping another of the adjacent vertebral bodies; and
   wherein said bone anchors comprise bone screws extending through said first and second openings for engaging said plate to the adjacent vertebral bodies.

* * * * *

UNITED STATES PATENT AND TRADEMARK OFFICE
CERTIFICATE OF CORRECTION

PATENT NO. : 7,621,938 B2 Page 1 of 1
APPLICATION NO. : 10/757819
DATED : November 24, 2009
INVENTOR(S) : Fred J. Molz, IV It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 828 days.

Signed and Sealed this

Twenty-sixth Day of October, 2010

David J. Kappos
*Director of the United States Patent and Trademark Office*